United States Patent
Xu et al.

(10) Patent No.: US 11,520,757 B2
(45) Date of Patent: Dec. 6, 2022

(54) EXPLANATIVE ANALYSIS FOR RECORDS WITH MISSING VALUES

(71) Applicant: International Business Machines Corporation, Armonk, NY (US)

(72) Inventors: Jing James Xu, Xian (CN); Jing Xu, Xian (CN); Xiao Ming Ma, Xian (CN); Jian Jun Wang, Xian (CN); Jun Wang, Xian (CN); A Peng Zhang, Xian (CN); Xing Wei, Xian (CN)

(73) Assignee: International Business Machines Corporation, Armonk, NY (US)

(*) Notice: Subject to any disclaimer, the term of this patent is extended or adjusted under 35 U.S.C. 154(b) by 95 days.

(21) Appl. No.: 17/019,383

(22) Filed: Sep. 14, 2020

(65) Prior Publication Data

US 2022/0083519 A1  Mar. 17, 2022

(51) Int. Cl.

| | |
|---|---|
| G06F 16/00 | (2019.01) |
| G06F 16/215 | (2019.01) |
| G06F 16/21 | (2019.01) |
| G06N 5/04 | (2006.01) |
| G06F 16/2457 | (2019.01) |
| G16H 10/60 | (2018.01) |

(52) U.S. Cl.
CPC ......... G06F 16/215 (2019.01); G06F 16/219 (2019.01); G06F 16/24573 (2019.01); G06N 5/045 (2013.01); G16H 10/60 (2018.01)

(58) Field of Classification Search
None
See application file for complete search history.

(56) References Cited

U.S. PATENT DOCUMENTS

2014/0100989 A1* 4/2014 Zhang ............... G06Q 30/0283
                                                              705/26.61
2019/0129819 A1   5/2019 Guo
(Continued)

OTHER PUBLICATIONS

"Multiple Imputation for Missing Data," Statistics Solution, accessed Sep. 11, 2020, 4 pages. <https://www.statisticssolutions.com/multiple-imputation-for-missing-data/>.

(Continued)

*Primary Examiner* — Bai D Vu
(74) *Attorney, Agent, or Firm* — Richard B. Thomas

(57) ABSTRACT

Embodiments relate to a system, computer program product, and method for determining missing values in respective data records with an explanatory analysis to provide a context of the determined values. Such method includes receiving a dataset including incomplete data records that are missing predictors and complete data records. A model is trained with the complete data records and candidate predictors for the missing predictors are generated. A predictor importance value is generated for each candidate predictor and the candidate predictors that have a predictor importance value in excess of a first threshold value are promoted. Respective promoted candidate predictors are inserted into the respective incomplete data records, thereby creating tentative data records. The tentative data records are injected into the model, a fit value is determined for each of the tentative data records, and a tentative data record with a fit value exceeding a second threshold value is selected.

20 Claims, 10 Drawing Sheets

(56) References Cited

U.S. PATENT DOCUMENTS

2019/0391968 A1 12/2019 Zoll
2020/0089173 A1 3/2020 Hazard

OTHER PUBLICATIONS

Abidin et al., "Performance Analysis of Machine Learning Algorithms for Missing Value Imputation," (IJACSA) International Journal of Advanced Computer Science and Applications, vol. 9, No. 6, 2018, pp. 442-447.
Mell et al., "The NIST Definition of Cloud Computing," Recommendations of the National Institute of Standards and Technology, U.S. Department of Commerce, Special Publication 800-145, Sep. 2011, 7 pages.
Ribeiro et al., "'Why Should I Trust You?' Explaining the Predictions of Any Classifier," (KDD '16) Proceedings of the 22nd ACM SIGKKD International Conference on Knowledge Discovery and Data Mining, Aug. 2016, pp. 1135-1144. <https://doi.org/10.1145/2939672.2939778>.
Royston, "Multiple Imputation of Missing Values," The Strata Journal, vol. 4, Issue 3, Aug. 1, 2004, pp. 227-241. <https://journals.sagepub.com/doi/10.1177/1536867X0400400301>.
Zhang et al., "Generating Personalized Recommendations to Address a Target Problem," U.S. Appl. No. 16/559,395, filed Sep. 3, 2019.

* cited by examiner

500

| Data Table A |||||
|---|---|---|---|---|
| Measured Item | Before Value(s) | After Value(s) | Units | Effects |
| Heart Rate | 83 | 72 | BPM | Decrease |
| Blood Pressure | 125/75/87 | 135/73/88 | mmHg | Increase |
| Superior Vena Cava (SVC) | 5 | ???????? | mmHg | Increase |
| Right Atrial Pressure (RAP) | 10/7/6 | 9/8/5 | mmHg | Decrease |
| Right Ventricular Pressure (RVP) | 75/0/10 | 62/0/7 | mmHg | Decrease |
| Pulmonary Artery Pressure (PAP) | 75/77/43 | 63/18/36 | mmHg | Decease |
| ... | ... | ... | ... | ... |

Continuous (Normal) Field Distribution Example

| Value | % | Count |
|---|---|---|
| A | 6.92 | 11 |
| B | 6.92 | 11 |
| C | 5.66 | 9 |
| D | 5.66 | 9 |
| E | 5.66 | 9 |
| F | 4.4 | 7 |
| G | 4.4 | 7 |
| H | 4.4 | 7 |
| I | 3.77 | 6 |
| J | 3.77 | 6 |
| K | 3.77 | 6 |
| L | 3.77 | 6 |
| M | 3.77 | 6 |
| N | 3.77 | 6 |
| O | 3.14 | 5 |
| P | 3.14 | 5 |
| Q | 3.14 | 5 |
| R | 2.52 | 4 |
| S | 2.52 | 4 |

Categorical Field Distribution Example

FIG. 8

Best Fit Example

| Age | Gender | BP | Drug | Classification Probability |
|---|---|---|---|---|
| 50 | F | Normal | Drug Y | 0.988 |
| 56 | M | Low | Drug Y | 0.988 |
| 60 | M | Normal | Drug Y | 0.985 |
| 41 | M | High | Drug Y | 0.983 |
| 39 | F | Normal | Drug Y | 0.969 |
| 50 | M | Normal | Drug Y | 0.956 |
| 36 | F | High | Drug Y | 0.955 |
| 74 | M | High | Drug Y | 0.943 |
| 16 | F | High | Drug Y | 0.937 |

FIG. 10

Worst Fit Example

| Age | Gender | BP | Drug | Classification Probability |
|---|---|---|---|---|
| 72 | F | Low | Drug X | 0.309 |
| 53 | M | Normal | Drug X | 0.180 |
| 57 | F | Normal | Drug X | 0.037 |
| 59 | F | Normal | Drug X | 0.016 |
| 23 | M | Normal | Drug X | 0.015 |
| 39 | M | Low | Drug X | 0.014 |
| 65 | F | High | Drug X | 0.012 |

FIG. 11

EXPLANATIVE ANALYSIS FOR RECORDS WITH MISSING VALUES

BACKGROUND

The present disclosure relates to determining missing values in data records, and, more specifically, to providing the missing values in the respective data records with an explanatory analysis to provide the context of the provided values.

Many known cognitive systems, including machine learning (ML) and artificial intelligence (AI) platforms, are built through end-to-end human intensive tasks that require highly skilled individuals to build the models and place them into production. The data gathering process for the information that will be used to build the respective models typically requires the respective builders to be fully familiar with the details of the initial datasets, including the quality, quantity, and completeness of the data. In some instances, the data records identified by the builders are incomplete with respect to maintaining a complete set of data therein. There are a number of known reasons for the missing values, including, improper transfer of data, record corruption, and non-collection of the data. Prior to using the affected data records for model building and prediction generation, at least one known mechanism for determining values for the missing data includes manually imputing the missing data values prior to proceeding with model building and prediction. In addition, there are a number of imputation methods that provide varying results.

SUMMARY

A system, computer program product, and method are provided for determining missing values in respective data records with an explanatory analysis to provide a context of the determined values.

In one aspect, a computer system is provided for determining missing values in respective data records with an explanatory analysis to provide a context of the determined values. The system includes one or more processing devices and at least one memory device operably coupled to the one or more processing device. The one or more processing devices are configured to receive a dataset that includes a plurality of data records therein. The data records include one or more data records that are incomplete data records missing one or more predictors and one or more data records that are complete data records. The one or more processing devices are also configured to train a model with at least a portion of the one or more complete data records and generate one or more candidate predictors for the one or more missing predictors. The one or more processing devices are further configured to determine a predictor importance value for each candidate predictor of the one or more candidate predictors and promote a portion of the candidate predictors that has a predictor importance value in excess of a first threshold value. The one or more processing devices are also configured to insert one or more respective promoted candidate predictors into the respective one or more incomplete data records, thereby creating one or more tentative data records. The one or more processing devices are further configured to inject the one or more tentative data records into the model, determine a fit value for each of the one or more tentative data records, and select a tentative data record with a fit value exceeding a second threshold value.

In another aspect, a computer program product is provided for determining missing values in respective data records with an explanatory analysis to provide a context of the determined values. The computer program product includes one or more computer readable storage media, and program instructions collectively stored on the one or more computer storage media. The product also includes program instructions to receive a dataset, the dataset including a plurality of data records therein. The data records include one or more data records that are incomplete data records missing one or more predictors and one or more data records that are complete data records. The product further includes program instructions to train a model with at least a portion of the one or more complete data records, and to generate one or more candidate predictors for the one or more missing predictors. The product also includes program instructions to determine a predictor importance value for each candidate predictor of the one or more candidate predictors and promote a portion of the candidate predictors that has a predictor importance value in excess of a first threshold value. The product further includes program instructions to insert one or more respective promoted candidate predictors into the respective one or more incomplete data records, thereby creating one or more tentative data records. The product also includes program instructions to inject the one or more tentative data records into the model, determine a fit value for each of the one or more tentative data records, and program instructions to select a tentative data record with a fit value exceeding a second threshold value.

In yet another aspect, a computer-implemented method is provided for determining missing values in respective data records with an explanatory analysis to provide a context of the determined values. The method includes receiving a dataset, the dataset including a plurality of data records therein. The data records include one or more data records that are incomplete data records missing one or more predictors and one or more data records that are complete data records. The method includes training a model with at least a portion of the one or more complete data records and generating one or more candidate predictors for the one or more missing predictors. The method also includes determining a predictor importance value for each candidate predictor of the one or more candidate predictors and promoting a portion of the candidate predictors that has a predictor importance value in excess of a first threshold value. The method also includes inserting one or more respective promoted candidate predictors into the respective one or more incomplete data records, thereby creating one or more tentative data records. The method further includes injecting the one or more tentative data records into the model, determining a fit value for each of the one or more tentative data records, and selecting a tentative data record with a fit value exceeding a second threshold value.

The present Summary is not intended to illustrate each aspect of, every implementation of, and/or every embodiment of the present disclosure. These and other features and advantages will become apparent from the following detailed description of the present embodiment(s), taken in conjunction with the accompanying drawings.

BRIEF DESCRIPTION OF THE DRAWINGS

The drawings included in the present application are incorporated into, and form part of, the specification. They illustrate embodiments of the present disclosure and, along with the description, serve to explain the principles of the disclosure. The drawings are illustrative of certain embodiments and do not limit the disclosure.

FIG. 5 is a tabular diagram illustrating a first example of a data table, in accordance with some embodiments of the present disclosure.

FIG. 8 is a tabular diagram illustrating an example of a categorical field distribution, in accordance with some embodiments of the present disclosure.

FIG. 10 is a tabular diagram illustrating a best fit example ranking, in accordance with some embodiments of the present disclosure.

FIG. 11 is a tabular diagram illustrating a worst fit example ranking, in accordance with some embodiments of the present disclosure.

Figure 1:
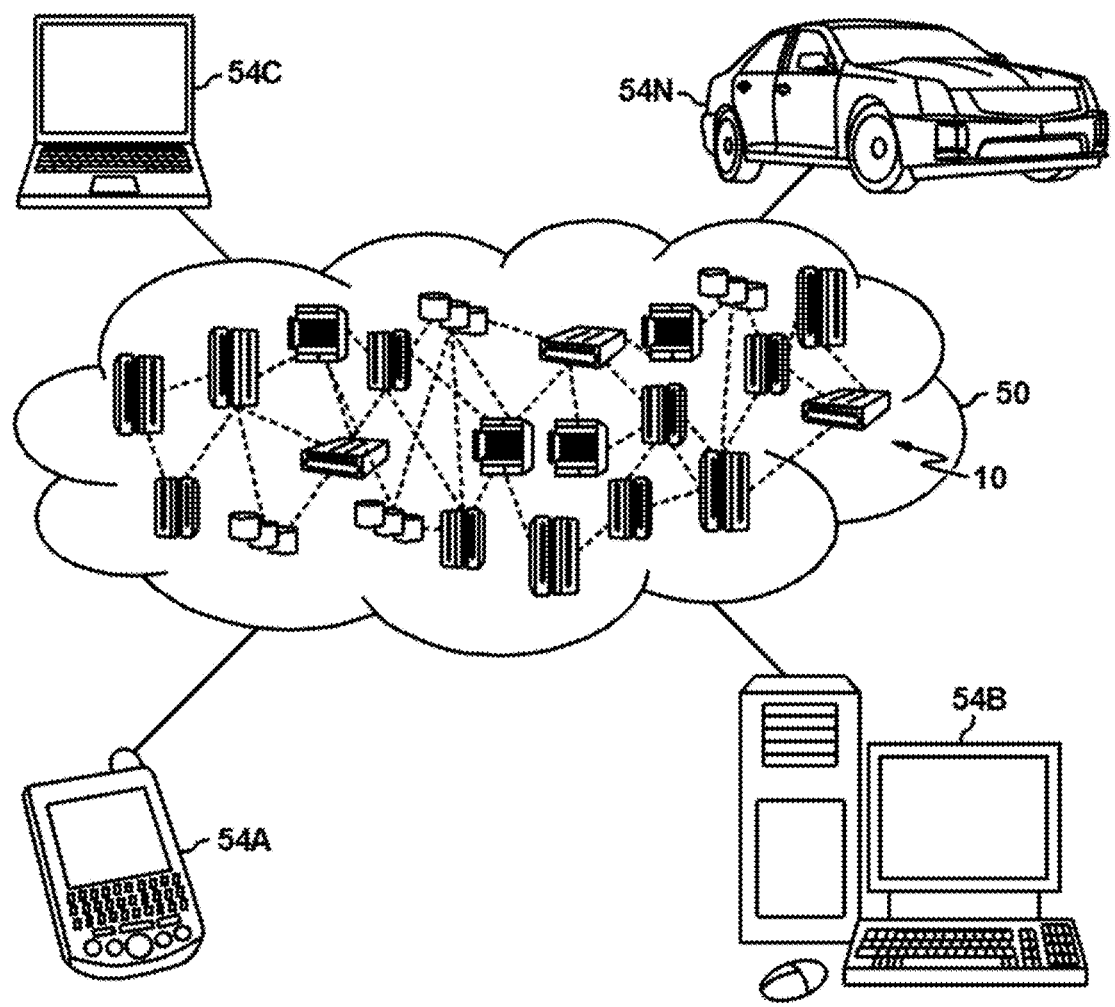
FIG. 1 is a schematic diagram illustrating a cloud computer environment, in accordance with some embodiments of the present disclosure.

While the present disclosure is amenable to various modifications and alternative forms, specifics thereof have been shown by way of example in the drawings and will be described in detail. It should be understood, however, that the intention is not to limit the present disclosure to the particular embodiments described. On the contrary, the intention is to cover all modifications, equivalents, and alternatives falling within the spirit and scope of the present disclosure.

DETAILED DESCRIPTION

It will be readily understood that the components of the present embodiments, as generally described and illustrated in the Figures herein, may be arranged and designed in a wide variety of different configurations. Thus, the following detailed description of the embodiments of the apparatus, system, method, and computer program product of the present embodiments, as presented in the Figures, is not intended to limit the scope of the embodiments, as claimed, but is merely representative of selected embodiments.

Reference throughout this specification to "a select embodiment," "at least one embodiment," "one embodiment," "another embodiment," "other embodiments," or "an embodiment" and similar language means that a particular feature, structure, or characteristic described in connection with the embodiment is included in at least one embodiment. Thus, appearances of the phrases "a select embodiment," "at least one embodiment," "in one embodiment," "another embodiment," "other embodiments," or "an embodiment" in various places throughout this specification are not necessarily referring to the same embodiment.

The illustrated embodiments will be best understood by reference to the drawings, wherein like parts are designated by like numerals throughout. The following description is intended only by way of example, and simply illustrates certain selected embodiments of devices, systems, and processes that are consistent with the embodiments as claimed herein.

It is to be understood that although this disclosure includes a detailed description on cloud computing, implementation of the teachings recited herein are not limited to a cloud computing environment. Rather, embodiments of the present disclosure are capable of being implemented in conjunction with any other type of computing environment now known or later developed.

Cloud computing is a model of service delivery for enabling convenient, on-demand network access to a shared pool of configurable computing resources (e.g., networks, network bandwidth, servers, processing, memory, storage, applications, virtual machines, and services) that can be rapidly provisioned and released with minimal management effort or interaction with a provider of the service. This cloud model may include at least five characteristics, at least three service models, and at least four deployment models.

Characteristics are as follows.

On-demand self-service: a cloud consumer can unilaterally provision computing capabilities, such as server time and network storage, as needed automatically without requiring human interaction with the service's provider.

Broad network access: capabilities are available over a network and accessed through standard mechanisms that promote use by heterogeneous thin or thick client platforms (e.g., mobile phones, laptops, and PDAs).

Resource pooling: the provider's computing resources are pooled to serve multiple consumers using a multi-tenant model, with different physical and virtual resources dynamically assigned and reassigned according to demand. There is a sense of location independence in that the consumer generally has no control or knowledge over the exact location of the provided resources but may be able to specify location at a higher level of abstraction (e.g., country, state, or datacenter).

Rapid elasticity: capabilities can be rapidly and elastically provisioned, in some cases automatically, to quickly scale out and rapidly released to quickly scale in. To the consumer, the capabilities available for provisioning often appear to be unlimited and can be purchased in any quantity at any time.

Measured service: cloud systems automatically control and optimize resource use by leveraging a metering capability at some level of abstraction appropriate to the type of service (e.g., storage, processing, bandwidth, and active user accounts). Resource usage can be monitored, controlled, and reported, providing transparency for both the provider and consumer of the utilized service.

Service Models are as follows.

Software as a Service (SaaS): the capability provided to the consumer is to use the provider's applications running on a cloud infrastructure. The applications are accessible from various client devices through a thin client interface such as a web browser (e.g., web-based e-mail). The consumer does not manage or control the underlying cloud infrastructure including network, servers, operating systems, storage, or even individual application capabilities, with the possible exception of limited user-specific application configuration settings.

Platform as a Service (PaaS): the capability provided to the consumer is to deploy onto the cloud infrastructure consumer-created or acquired applications created using programming languages and tools supported by the provider. The consumer does not manage or control the underlying cloud infrastructure including networks, servers, operating systems, or storage, but has control over the deployed applications and possibly application hosting environment configurations.

Infrastructure as a Service (IaaS): the capability provided to the consumer is to provision processing, storage, networks, and other fundamental computing resources where the consumer is able to deploy and run arbitrary software, which can include operating systems and applications. The consumer does not manage or control the underlying cloud infrastructure but has control over operating systems, storage, deployed applications, and possibly limited control of select networking components (e.g., host firewalls).

Deployment Models are as follows.

Private cloud: the cloud infrastructure is operated solely for an organization. It may be managed by the organization or a third party and may exist on-premises or off-premises.

Community cloud: the cloud infrastructure is shared by several organizations and supports a specific community that has shared concerns (e.g., mission, security requirements, policy, and compliance considerations). It may be managed by the organizations or a third party and may exist on-premises or off-premises.

Public cloud: the cloud infrastructure is made available to the general public or a large industry group and is owned by an organization selling cloud services.

Hybrid cloud: the cloud infrastructure is a composition of two or more clouds (private, community, or public) that remain unique entities but are bound together by standardized or proprietary technology that enables data and application portability (e.g., cloud bursting for load-balancing between clouds).

A cloud computing environment is service oriented with a focus on statelessness, low coupling, modularity, and semantic interoperability. At the heart of cloud computing is an infrastructure that includes a network of interconnected nodes.

Referring now to FIG. 1, illustrative cloud computing environment 50 is depicted. As shown, cloud computing environment 50 includes one or more cloud computing nodes 10 with which local computing devices used by cloud consumers, such as, for example, personal digital assistant (PDA) or cellular telephone 54A, desktop computer 54B, laptop computer 54C, and/or automobile computer system 54N may communicate. Nodes 10 may communicate with one another. They may be grouped (not shown) physically or virtually, in one or more networks, such as Private, Community, Public, or Hybrid clouds as described hereinabove, or a combination thereof. This allows cloud computing environment 50 to offer infrastructure, platforms and/or software as services for which a cloud consumer does not need to maintain resources on a local computing device. It is understood that the types of computing devices 54A-N shown in FIG. 1 are intended to be illustrative only and that computing nodes 10 and cloud computing environment 50 can communicate with any type of computerized device over any type of network and/or network addressable connection (e.g., using a web browser).

Figure 2:
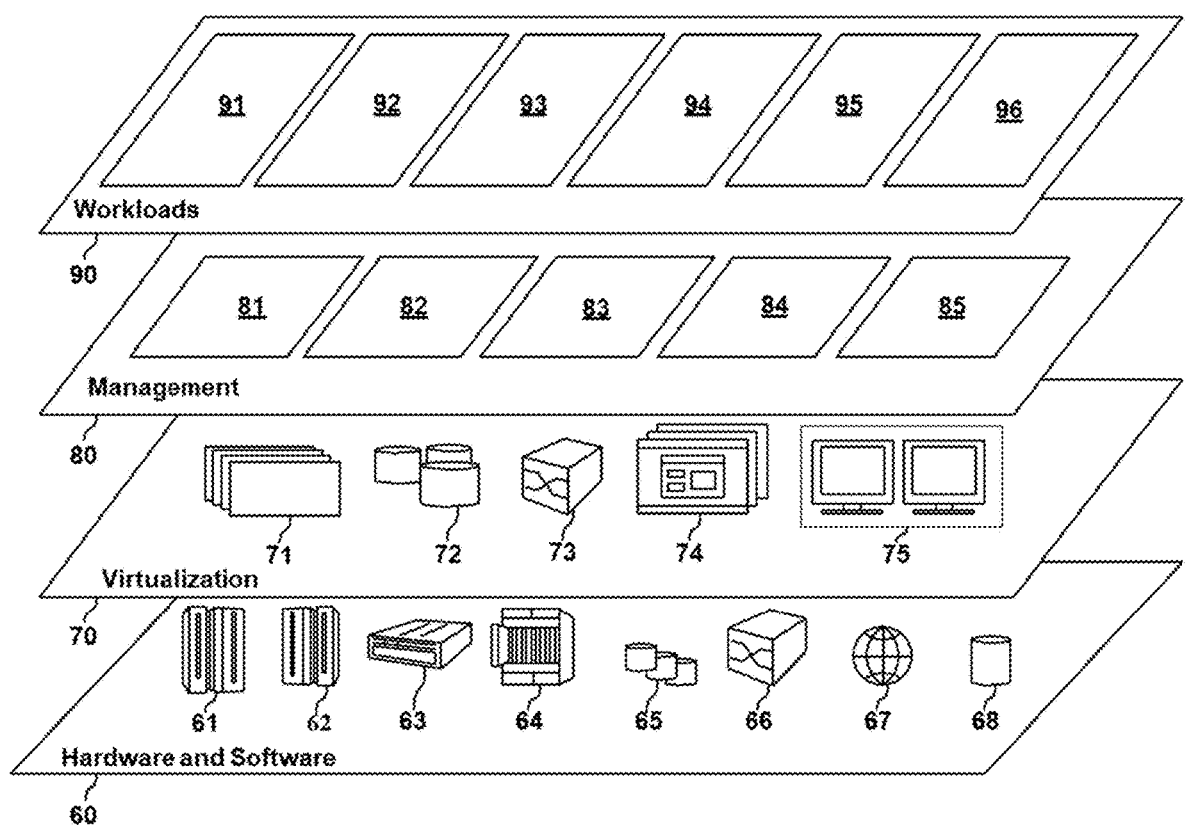
FIG. 2 is a block diagram illustrating a set of functional abstraction model layers provided by the cloud computing environment, in accordance with some embodiments of the present disclosure.

Referring now to FIG. 2, a set of functional abstraction layers provided by cloud computing environment 50 (FIG. 1) is shown. It should be understood in advance that the components, layers, and functions shown in FIG. 2 are intended to be illustrative only and embodiments of the disclosure are not limited thereto. As depicted, the following layers and corresponding functions are provided:

Hardware and software layer 60 includes hardware and software components. Examples of hardware components include: mainframes 61; RISC (Reduced Instruction Set Computer) architecture based servers 62; servers 63; blade servers 64; storage devices 65; and networks and networking components 66. In some embodiments, software components include network application server software 67 and database software 68.

Virtualization layer 70 provides an abstraction layer from which the following examples of virtual entities may be provided: virtual servers 71; virtual storage 72; virtual networks 73, including virtual private networks; virtual applications and operating systems 74; and virtual clients 75.

In one example, management layer 80 may provide the functions described below. Resource provisioning 81 provides dynamic procurement of computing resources and other resources that are utilized to perform tasks within the cloud computing environment. Metering and Pricing 82 provide cost tracking as resources are utilized within the cloud computing environment, and billing or invoicing for consumption of these resources. In one example, these resources may include application software licenses. Security provides identity verification for cloud consumers and tasks, as well as protection for data and other resources. User portal 83 provides access to the cloud computing environment for consumers and system administrators. Service level management 84 provides cloud computing resource allocation and management such that required service levels are met. Service Level Agreement (SLA) planning and fulfillment 85 provide pre-arrangement for, and procurement of, cloud computing resources for which a future requirement is anticipated in accordance with an SLA.

Workloads layer 90 provides examples of functionality for which the cloud computing environment may be utilized. Examples of workloads and functions which may be provided from this layer include: mapping and navigation 91; software development and lifecycle management 92; virtual classroom education delivery 93; data analytics processing 94; transaction processing 95; and determining missing values in respective data records with an explanatory analysis to provide a context of the determined values 96.

Figure 3:
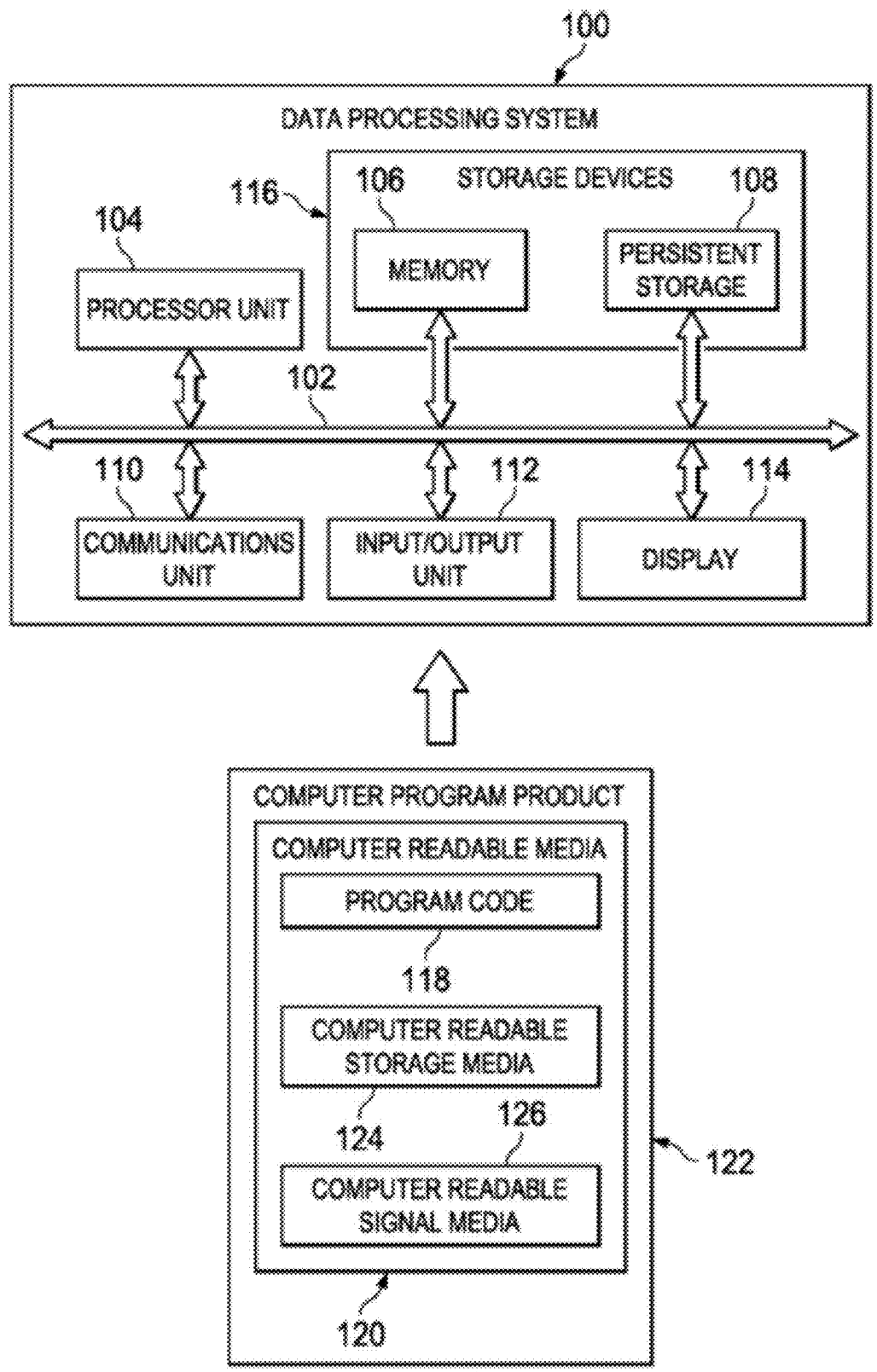
FIG. 3 is a block diagram illustrating a computer system/server that may be used as a cloud-based support system, to implement the processes described herein, in accordance with some embodiments of the present disclosure.

Referring to FIG. 3, a block diagram of an example data processing system, hereon referred to as computer system 100 is provided. system 100 may be embodied in a computer system/server in a single location, or in at least one embodiment, may be configured in a cloud-based system sharing computing resources. For example, and without limitation, the computer system 100 may be used as a cloud computing node 10.

Aspects of the computer system 100 may be embodied in a computer system/server in a single location, or in at least one embodiment, may be configured in a cloud-based system sharing computing resources as a cloud-based support system, to implement the system, tools, and processes described herein. The computer system 100 is operational with numerous other general purpose or special purpose computer system environments or configurations. Examples of well-known computer systems, environments, and/or configurations that may be suitable for use with the computer system 100 include, but are not limited to, personal computer systems, server computer systems, thin clients, thick clients, hand-held or laptop devices, multiprocessor systems, microprocessor-based systems, set top boxes, programmable consumer electronics, network PCs, minicomputer systems, mainframe computer systems, and file systems (e.g., distributed storage environments and distributed cloud computing environments) that include any of the above systems, devices, and their equivalents.

The computer system 100 may be described in the general context of computer system-executable instructions, such as program modules, being executed by The computer system 100. Generally, program modules may include routines, programs, objects, components, logic, data structures, and so on that perform particular tasks or implement particular abstract data types. The computer system 100 may be practiced in distributed cloud computing environments where tasks are performed by remote processing devices that are linked through a communications network. In a distributed cloud computing environment, program modules may be located in both local and remote computer system storage media including memory storage devices.

As shown in FIG. 3, the computer system 100 is shown in the form of a general-purpose computing device. The components of the computer system 100 may include, but are not limited to, one or more processors or processing devices 104 (sometimes referred to as processors and processing units), e.g., hardware processors, a system memory 106, and a communications bus 102 that couples various system components including the system memory 106 to the processing device 104. The communications bus 102 represents one or more of any of several types of bus structures, including a memory bus or memory controller, a peripheral bus, an accelerated graphics port, and a processor or local bus using any of a variety of bus architectures. By way of example, and not limitation, such architectures include Industry Standard Architecture (ISA) bus, Micro Channel Architecture (MCA) bus, Enhanced ISA (EISA) bus, Video Electronics Standards Association (VESA) local bus, and Peripheral Component Interconnects (PCI) bus. The computer system 100 typically includes a variety of computer system readable media. Such media may be any available media that is accessible by the computer system 100 and it includes both volatile and non-volatile media, removable and non-removable media. In addition, the computer system 100 may include one or more persistent storage devices 108, communications units 110, input/output (I/O) units 112, and displays 114.

The processing device 104 serves to execute instructions for software that may be loaded into the system memory 106. The processing device 104 may be a number of processors, a multi-core processor, or some other type of processor, depending on the particular implementation. A number, as used herein with reference to an item, means one or more items. Further, the processing device 104 may be implemented using a number of heterogeneous processor systems in which a main processor is present with secondary processors on a single chip. As another illustrative example, the processing device 104 may be a symmetric multiprocessor system containing multiple processors of the same type.

The system memory 106 and persistent storage 108 are examples of storage devices 116. A storage device may be any piece of hardware that is capable of storing information, such as, for example without limitation, data, program code in functional form, and/or other suitable information either on a temporary basis and/or a permanent basis. The system memory 106, in these examples, may be, for example, a random access memory or any other suitable volatile or non-volatile storage device. The system memory 106 can include computer system readable media in the form of volatile memory, such as random access memory (RAM) and/or cache memory.

The persistent storage 108 may take various forms depending on the particular implementation. For example, the persistent storage 108 may contain one or more components or devices. For example, and without limitation, the persistent storage 108 can be provided for reading from and writing to a non-removable, non-volatile magnetic media (not shown and typically called a "hard drive"). Although not shown, a magnetic disk drive for reading from and writing to a removable, non-volatile magnetic disk (e.g., a "floppy disk"), and an optical disk drive for reading from or writing to a removable, non-volatile optical disk such as a CD-ROM, DVD-ROM or other optical media can be provided. In such instances, each can be connected to the communication bus 102 by one or more data media interfaces.

The communications unit 110 in these examples may provide for communications with other computer systems or devices. In these examples, the communications unit 110 is a network interface card. The communications unit 110 may provide communications through the use of either or both physical and wireless communications links.

The input/output unit 112 may allow for input and output of data with other devices that may be connected to the computer system 100. For example, the input/output unit 112 may provide a connection for user input through a keyboard, a mouse, and/or some other suitable input device. Further, the input/output unit 112 may send output to a printer. The display 114 may provide a mechanism to display information to a user. Examples of the input/output units 112 that facilitate establishing communications between a variety of devices within the computer system 100 include, without limitation, network cards, modems, and input/output interface cards. In addition, the computer system 100 can communicate with one or more networks such as a local area network (LAN), a general wide area network (WAN), and/or a public network (e.g., the Internet) via a network adapter (not shown in FIG. 3). It should be understood that although not shown, other hardware and/or software components could be used in conjunction with the computer system 100. Examples of such components include, but are not limited to: microcode, device drivers, redundant processing units, external disk drive arrays, RAID systems, tape drives, and data archival storage systems.

Instructions for the operating system, applications and/or programs may be located in the storage devices 116, which are in communication with the processing device 104 through the communications bus 102. In these illustrative examples, the instructions are in a functional form on the persistent storage 108. These instructions may be loaded into the system memory 106 for execution by the processing device 104. The processes of the different embodiments may be performed by the processing device 104 using computer implemented instructions, which may be located in a memory, such as the system memory 106. These instructions are referred to as program code, computer usable program code, or computer readable program code that may be read and executed by a processor in the processing device 104. The program code in the different embodiments may be embodied on different physical or tangible computer readable media, such as the system memory 106 or the persistent storage 108.

The program code 118 may be located in a functional form on the computer readable media 120 that is selectively removable and may be loaded onto or transferred to the computer system 100 for execution by the processing device 104. The program code 118 and computer readable media 120 may form a computer program product 122 in these examples. In one example, the computer readable media 120 may be computer readable storage media 124 or computer readable signal media 126. Computer readable storage media 124 may include, for example, an optical or magnetic disk that is inserted or placed into a drive or other device that is part of the persistent storage 108 for transfer onto a storage device, such as a hard drive, that is part of the persistent storage 108. The computer readable storage media 124 also may take the form of a persistent storage, such as a hard drive, a thumb drive, or a flash memory, that is connected to the computer system 100. In some instances, the computer readable storage media 124 may not be removable from the computer system 100.

Alternatively, the program code 118 may be transferred to the computer system 100 using the computer readable signal media 126. The computer readable signal media 126 may be, for example, a propagated data signal containing the program code 118. For example, the computer readable signal media 126 may be an electromagnetic signal, an optical signal, and/or any other suitable type of signal. These signals may be transmitted over communications links, such as wireless communications links, optical fiber cable, coaxial cable, a wire, and/or any other suitable type of communications link. In other words, the communications link and/or the connection may be physical or wireless in the illustrative examples.

In some illustrative embodiments, the program code 118 may be downloaded over a network to the persistent storage 108 from another device or computer system through the computer readable signal media 126 for use within the computer system 100. For instance, program code stored in a computer readable storage medium in a server computer system may be downloaded over a network from the server to the computer system 100. The computer system providing the program code 118 may be a server computer, a client computer, or some other device capable of storing and transmitting the program code 118.

The program code 118 may include one or more program modules (not shown in FIG. 3) that may be stored in system memory 106 by way of example, and not limitation, as well as an operating system, one or more application programs, other program modules, and program data. Each of the operating systems, one or more application programs, other program modules, and program data or some combination thereof, may include an implementation of a networking environment. The program modules of the program code 118 generally carry out the functions and/or methodologies of embodiments as described herein.

The different components illustrated for the computer system 100 are not meant to provide architectural limitations to the manner in which different embodiments may be implemented. The different illustrative embodiments may be implemented in a computer system including components in addition to or in place of those illustrated for the computer system 100.

The present disclosure may be a system, a method, and/or a computer program product at any possible technical detail level of integration. The computer program product may include a computer readable storage medium (or media) having computer readable program instructions thereon for causing a processor to carry out aspects of the present disclosure.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present disclosure may be assembler instructions, instruction-set-architecture (ISA) instructions, machine instructions, machine dependent instructions, microcode, firmware instructions, state-setting data, configuration data for integrated circuitry, or either source code or object code written in any combination of one or more programming languages, including an object oriented programming language such as Smalltalk, C++, or the like, and procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present disclosure.

Aspects of the present disclosure are described herein with reference to flowchart illustrations and/or block diagrams of methods, apparatus (systems), and computer program products according to embodiments of the disclosure. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present disclosure. In this regard, each block in the flowchart or block diagrams may represent a module, segment, or portion of instructions, which comprises one or more executable instructions for implementing the specified logical function(s). In some alternative implementations, the functions noted in the blocks may occur out of the order noted in the Figures. For example, two blocks shown in succession may, in fact, be accomplished as one step, executed concurrently, substantially concurrently, in a partially or wholly temporally overlapping manner, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

Many known cognitive systems, including machine learning (ML) and artificial intelligence (AI) platforms, are built through end-to-end human intensive tasks that require highly skilled individuals to build the models and place them into production. The data gathering process for the information that will be used to build the respective models typically requires the respective builders to be fully familiar with the details of the initial datasets, including the quality, quantity, and completeness of the data. Typically, the data is embedded within data tables, and more specifically, each value of data is maintained in a cell, a plurality of cells defining a record, and the data table included a plurality of data records.

In some instances, the data records identified by the builders are incomplete with respect to maintaining the data therein. There are a number of known reasons for the missing values, including, improper transfer of data, at least partial record corruption, and non-collection of the data. Prior to using the affected data records for model building and prediction generation, at least one known mechanism for determining values for the missing data includes imputing the missing data values prior to proceeding with model building and prediction. In addition, there are a number of imputation methods that provide varying results. In some cases, if there is insufficient data to impute with, imputation methods will not work. In addition to the imputation methods, knowledgeable individuals may want to employ "reasonable guesswork" or "professional estimate" to provide a value, where the reasonable guesswork includes some level of knowledge of the variability of the missing value with respect to itself and other variables, and any known constraints. In addition, reasonable guesswork may employ some known data, where the known data may be used to facilitate some mathematical derivation of the missing value, and may also employ any other information that may provide a justification of the estimated value. However, there are no mechanisms to prove the estimated, or hypothetical, value is reasonable accurate, and there is no support provided with respect as to how the substitute value for the missing real value will impact subsequent prediction results if the record, with the substitute value, is used to build a machine learning model therefore. In at least some instances, the affected data record will be discarded due no known mechanism to generate a reasonable substitute value, since attempting to train a machine learning model with incomplete data may negatively impact the training of the model.

A system, computer program product, and method are disclosed and described herein directed toward determining missing values in data records, and, more specifically, toward providing the missing values in the respective data records with an explanatory analysis to provide the context of the provided values. In at least some embodiments, data records used to train machine learning models are data records with "predictor variables," referred to as "predictors" hereon, and "target variables," hereon referred to as "targets." A predictor is a variable whose values will be used to predict the value of the target variable. It is analogous to the independent variables, e.g., variables typically found on the right side of the equal sign in mathematical expressions, such as a linear regression. In addition, a predictor may refer to each value within an individual cell in a data record. A target is a variable whose values are to be modeled and predicted by other variables, e.g., the predictors. It is analogous to the dependent variable, e.g., the variable typically found on the left side of the equal sign in mathematical expressions, such as a linear regression. Accordingly, the targets and predictors are used on a data record-by-data record basis, i.e., on a record-level basis.

In at least one embodiment, a first, i.e., initial dataset is received. The initial dataset includes a plurality of data records therein. One or more data records within the initial dataset are incomplete, i.e., one or more data records are missing one or more predictors. In addition, one or more data records within the initial dataset are complete, i.e., one or more data records are not missing any predictors. Accordingly, the data records in the initial dataset are divided into a complete data records subset and an incomplete data records subset on a record-level basis.

In at least some embodiments, the complete data records from the initial dataset, i.e., those data records in the complete data record subset, are selected to build a machine learning model, and those complete data records are injected into the model as a second data set, i.e., a complete data record dataset. Therefore, the complete data records may be used to build a missing predictor predictive model through one or more machine learning model building algorithms. This predictive model can present a pattern in the data records that may be helpful in finding accurate values for the missing predictors. The model includes the targets from the complete data records injected into, and ingested by, the model.

In one or more embodiments, the incomplete data records from the initial dataset, i.e., those data records in the incomplete data record subset, are selected for analysis. Specifically, at a record-level basis, for a data record with one or more missing values, i.e., missing predictors, a "feature space" for each missing value will be generated. The feature space will hold one or more sampling values that are generated as further described. For the given data record, several sampling values for each missing predictor are generated. A sampling values dataset will be created based on the combination of generated sampling values. In some embodiments, a field distribution for each field of non-missing values, i.e., predictors, is generated based on the non-missing predictors in the training data, i.e., the respective data records. In some embodiments, a normal distribution can be used to approximately fit a continuous field of the non-missing predictors, and a categorical value list with record-level percentages can be used to fit a categorical field of non-missing values. For the missed predictor in the respective data record, one or more sampling values from both of the continuous field and categorical field, that may potentially be prospective predictors, are collected within the feature space. Accordingly, on a record-level basis, sampling values that reasonably represent prospective values for the missing predictors are collected in the feature space, and these sampling values are referred to as candidate predictors.

The values of the candidate predictors populating the feature space are individually analyzed to determine a relative importance for each candidate predictor, thereby calculating a record-level predictor importance for each candidate predictor. In some embodiments, the analysis includes use of a Local Interpretable Model-agnostic Explanations algorithm, i.e., LIME. However, other ranking algorithms are within the scope of this disclosure. Each candidate predictor in the feature space is analyzed by LIME to generate the record-level predictor importance of each candidate predictor. The top number (N) of candidate predictors with the record-level predictor importance values above a predetermined first threshold value are promoted for downstream analysis as a potential value, i.e., there will be N promoted candidate predictors of the missed predictors that will be evaluated as candidates for the missing predictors. Accordingly, on a record-level basis, a subset of the candidate predictors in the feature space including promoted candidate predictors is maintained based on the importance thereof.

Those data records with the missing predictors are collected into a third dataset, i.e., an incomplete data record dataset. Each incomplete data record in the incomplete data record dataset receives the respective promoted top N candidate predictors in turn from the feature space. Specifically, the respective promoted candidate predictors are inserted into the respective cells having the missing predictors, thereby creating a plurality of tentative data records for each incomplete data record. The tentative data records are collected into a fourth dataset, i.e., a tentative data records dataset. The tentative data records from the tentative records dataset are injected into the missing predictor predictive model, and each tentative data record is scored by the model with respect to establishing how well the tentative data record fits with the complete data records used to train the model. For example, in some embodiments, the target of the tentative data record is embedded within the tentative data record, therefore the actual value for the target is known. The tentative data record is processed to provide a computed target that may be compared with the actual target. The closer the computed target is to the actual target, the greater the numerical value of the respective fit of the tentative data record with the complete data records within the respective data table. Accordingly, the fit results of each comparison generates a confidence value indicative of the inserted candidate predictors probability of being correct.

In some embodiments, once the confidence scores for fit for the tentative data records are collected on a record-level basis, the scores are ranked as a function of the fit. In some embodiments, a first subset of fit scores are determined to be "best fit" by comparing the respective fit scores with a predetermined second threshold value. Those tentative data records with fit scores in excess of the second threshold value will be identified as a best fit. Therefore, the most likely values for the missing predictors are identified, and the effect of the tentative values for the missing predictors on the operation of a model to make predictions is recorded.

In addition, the reliability of the reasoning, or proper guesswork detail, is automatically recorded to justify the inclusion of the tentative values, with a reasonable inference of good coverage with respect to the aforementioned, and respective, continuous and categorical fields. The respective candidate predictors embedded in the best fit data records will also be established, and documented, as best fit for the missing predictor candidate predictors. Accordingly, one or more explanatory features directed toward the identification of the one or more best fit data records as a function of the respective inserted one or more candidate predictors are recorded to preserve the selections thereof, including the effects of the candidate predictors on the performance of the model.

Similarly, in some embodiments, a second subset of fit scores are determined to be "worst fit" by comparing the respective fit scores with a third threshold value. Those tentative data records with fit scores below the third threshold value will be identified as a worst fit. Therefore, the least likely values for the missing predictors are identified, and the effect of the tentative values for the missing predictors on the operation of a model to make predictions may be recorded. In addition, the reliability of the reasoning, or proper guesswork detail, may be recorded to justify the exclusion of the tentative values, with a reasonable inference of poor coverage with respect to the aforementioned, and respective, continuous and categorical fields. The respective candidate predictors embedded in the worst fit data records will also be established, and documented, as worst fit for the missing predictor candidate predictors. Accordingly, one or more explanatory features directed toward the identification of the one or more worst fit data records as a function of the respective inserted one or more candidate predictors are recorded to preserve the denials of selection thereof, including any deleterious effects of the candidate predictors on the performance of the model.

Figure 4:
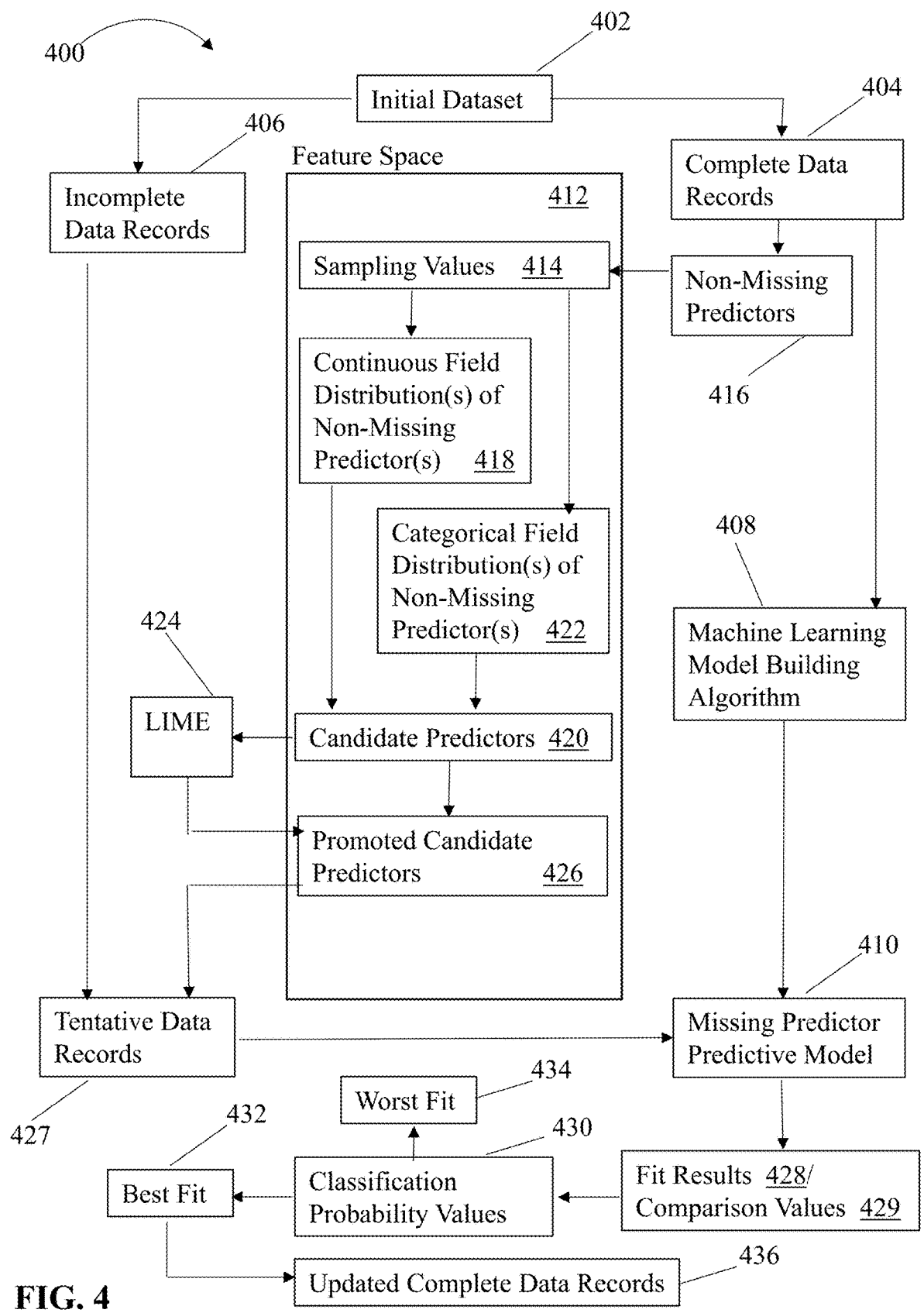
FIG. 4 is a high-level flowchart illustrating a process determining missing values in respective data records with an explanatory analysis to provide a context of the determined values, in accordance with some embodiments of the present disclosure.

Referring to FIG. 4, a high-level flow chart is provided illustrating a process 400 for determining missing values in respective data records with an explanatory analysis to provide a context of the determined values. In at least one embodiment, the process 400 is executed by the computer system 100 (as shown and described in FIG. 3). In at least one embodiment, a first, i.e., initial dataset 402 is received. The initial dataset 402 includes a plurality of data records therein. One or more data records within the initial dataset are incomplete, i.e., one or more data records are missing one or more predictors. In addition, one or more data records within the initial dataset are complete, i.e., one or more data records are not missing any predictors. Accordingly, the data records in the initial dataset 402 are divided into a complete data records 404 subset and an incomplete data records 406 subset on a record-level basis.

Referring to FIG. 5, a tabular diagram is provided illustrating a first example of a data table, i.e., a data table A 500. The data table 500 includes a plurality of data records 502, where the specific contents of each cell are not necessary to describe in detail herein. Each data record 502 includes one or more predictors 504 (two shown for each record 502 in FIG. 5) and at least one target 506. In the embodiment shown in FIG. 5, the before and after predictors 504 determine an "Effect" target 506. Notably, in one of the data records 502, a missing predictor 504 is found. Intuitively, since the "effect" for that particular data record 502 is "increase," the value to be placed in the respective cell for the missing predictor 508 would reasonably be great than "5." However, such intuition does not provide an actual value and no explanation. Accordingly, referring to FIGS. 4 and 5, the complete data records 404 subset includes at least the five data records 502 that are complete and the incomplete data records 406 subset includes at least the data record 502 that includes the missing predictor 508.

Figure 6:
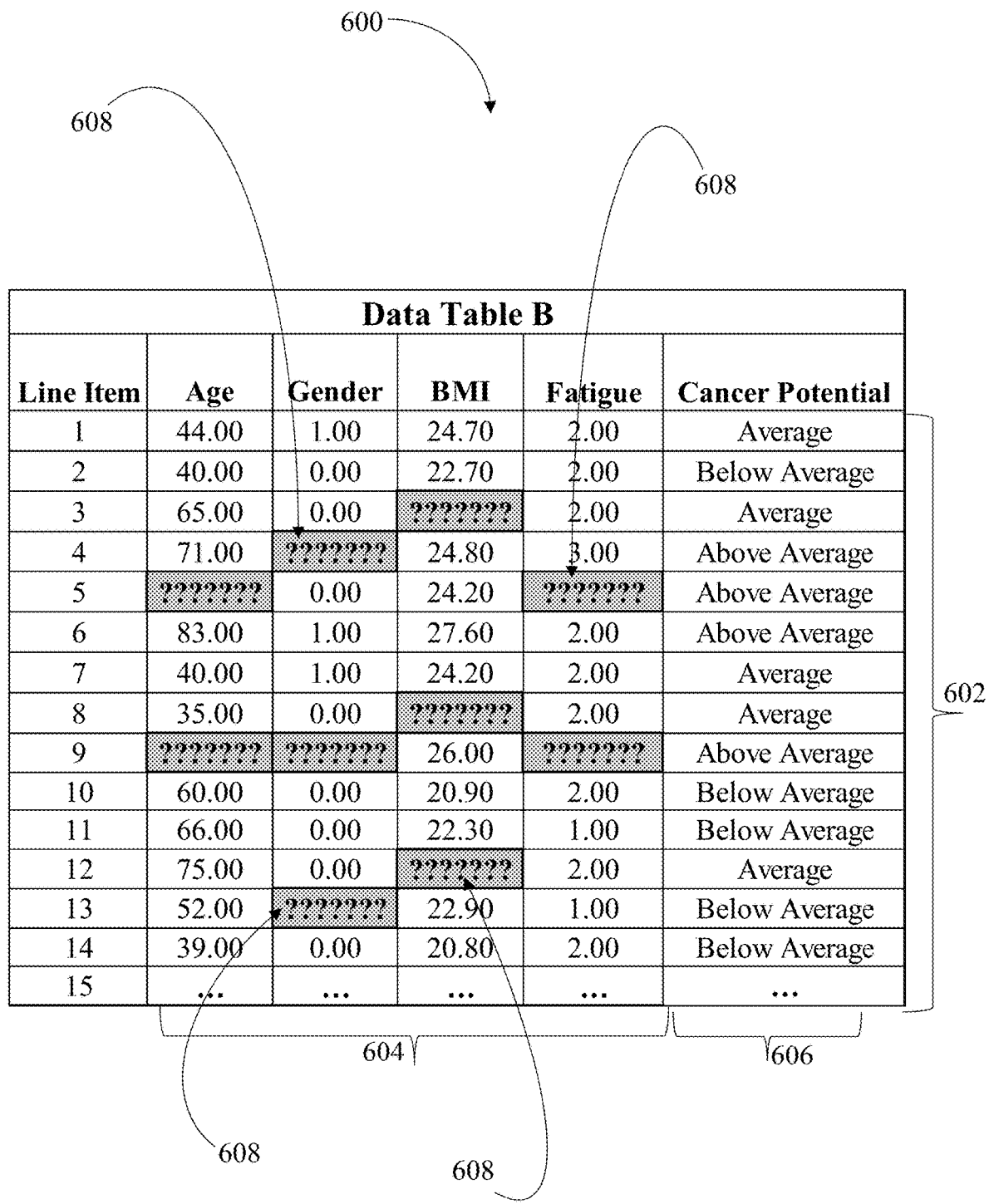
FIG. 6 is a tabular diagram illustrating a second example of a data table, in accordance with some embodiments of the present disclosure.

Referring to FIG. 6, a tabular diagram is provided illustrating a second example of a data table, i.e., a data table B 600. The data table 600 includes a plurality of data records 602, where the specific contents of each cell are not necessary to describe in detail herein. Each data record 602 includes one or more predictors 604 (four shown for each record 602 in FIG. 6) and at least one target 606. In the embodiment shown in FIG. 6, the "Age," "Gender," "BMI," and "Fatigue" predictors 604 determine a "Cancer Potential" target 606. Notably, a number of records 602 have missing predictors 608, where some records 602 have more than one missing predictor 608. Attempting to determine the values for each of the missing predictors 608 with sufficient documented reasoning for the values on a record-level basis will be a difficult task to execute. Accordingly, referring to FIGS. 4 and 6, the complete data records 404 subset includes at least the seven data records 602 that are complete and the incomplete data records 406 subset includes at least the seven data records 602 that includes the missing predictors 608.

Referring again to FIG. 4, in at least some embodiments, the complete data records 404 are selected to build a machine learning model, where those complete data records 404 are injected into a machine learning model building algorithm 408 to build a missing predictor predictive model 410. In some embodiments, the predictive model 410 can detect and present a pattern in the complete data records 404 that may be helpful in finding accurate values for the missing predictors 508 or 608 (as shown in FIGS. 5 and 6, respectively). The model 410 includes the targets 506 or 606 (as shown in FIGS. 5 and 6, respectively) from the complete data records 404 injected into, and ingested by, the model 410. In some embodiments, the computer system 100 (shown in FIG. 3) may execute the process 400 on multiple datasets 402 simultaneously. In general, herein, the process 400 is described as executing on a single dataset 402.

In one or more embodiments, the incomplete data records 406, i.e., those data records, e.g., either the data records 502 or the data records 602 (see FIGS. 5 and 6, respectively), in the incomplete data records 406 subset, are selected for analysis. Unless otherwise specified, the data table 600 of FIG. 6 will be referred to while describing the embodiments hereon. At a record-level basis, for a data record 602, i.e., an incomplete data record 406 with one or more missing predictors 608, i.e., missing predictors 608, a "feature space" 412 for each missing predictor 608 will be generated. Each feature space 412 is configured to hold one or more sampling values 414 therein that are generated as further described. In one or more embodiments, a single feature space 412 may be partitioned to emulate multiple feature spaces 412. For the given incomplete data record 406, several sampling values, i.e., a sampling values 414 dataset for each missing predictor 608 is generated as discussed further with reference to FIGS. 7 and 8.

Figure 7:
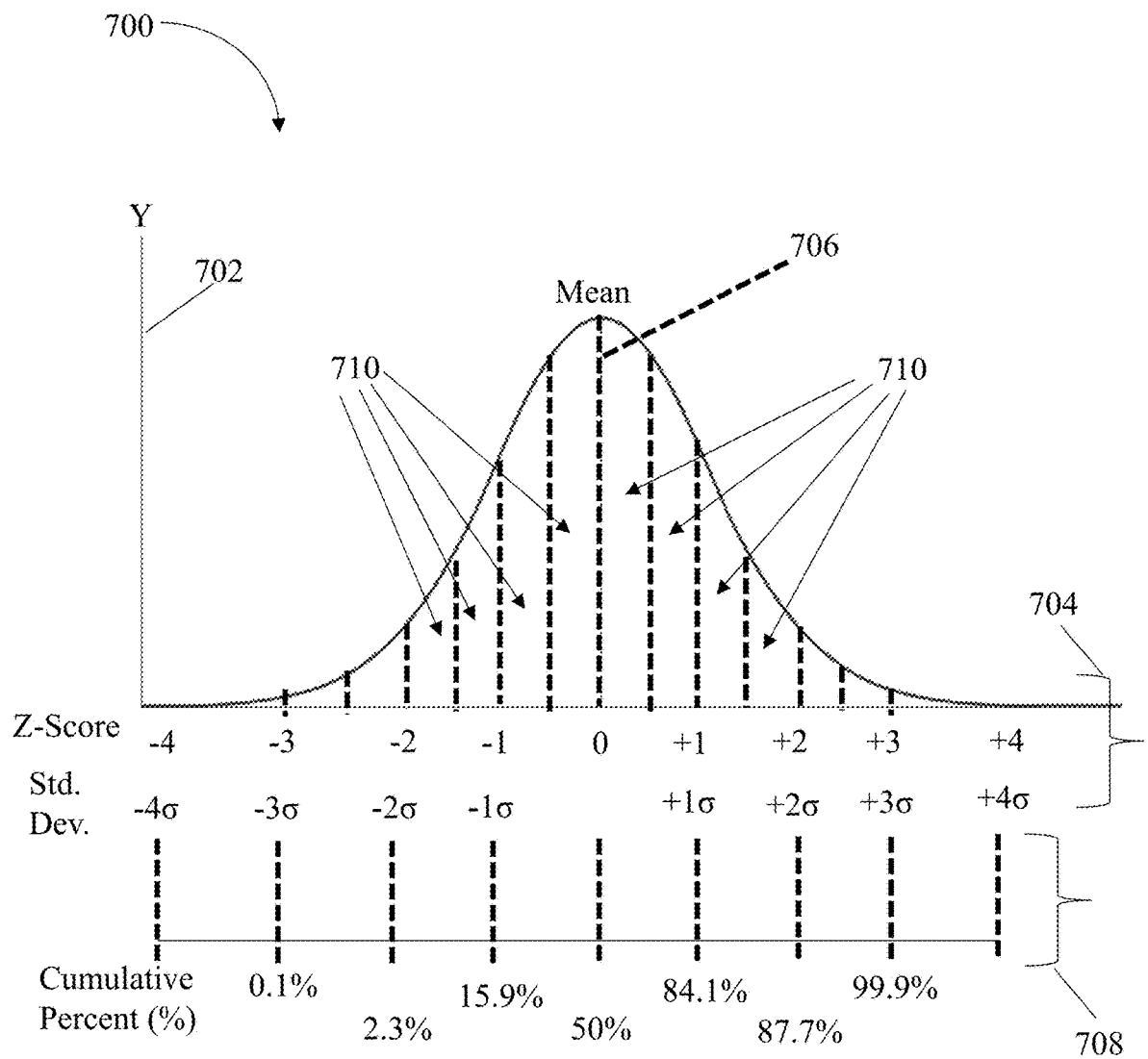
FIG. 7 is a graphical diagram illustrating an example of a continuous (normal) field distribution, in accordance with some embodiments of the present disclosure.

Referring to FIG. 7, a graphical diagram is provided illustrating an example of a continuous field distribution 700, in accordance with some embodiments of the present disclosure. Also referring to FIG. 4, in at least one embodiment, a normal, i.e., continuous field distribution 700 (labeled as 418 in FIG. 4) of sampling values 414 for each field of non-missing values, i.e., non-missing predictors 416, is generated based on the population of non-missing predictors 416 in the training data, i.e., the respective complete data records 404. In some embodiments, the continuous field distribution 700 can be used to fit a continuous field of the non-missing predictors 416. The continuous field distribution 700 includes an abscissa 702 (i.e., Y-axis 702) that represents the values of the subject measurements, in the instant case, the non-missing predictors 416. The continuous field distribution 700 also includes an ordinate 704 (i.e., X-axis 704) that represents the distance from a mean 706 value in units, or multiples of standard deviations, i.e., a extending from $-4\sigma$ to $+4\sigma$, where $0\sigma$ represents the mean 706, with a corresponding score of integers ranging from $-4$ to $+4$ defining the Z-score. A cumulative percent (%) bar 708 is provided to represent the cumulative percent of the values represented. The portion of the sampling values 414 generated from the continuous field distribution 700 are determined as mean $(706) \pm k \times \text{std. dev} + \epsilon$ to give a well coverage, where k is a parameter to set the size of sampling, e.g., in some embodiments, without limitation, within a Z-score range extending from about +3 and about +5 (not shown) to about $-3$ and about $-5$ (not shown), respectively, along the X-axis 704, and E is a random small noise value.

In at least some embodiments, the continuous field distribution 700 is divided into a plurality of "bins" 710. In the illustrated embodiment, the continuous field distribution 700 is divided into the bins 710 as a function of the integer values of the standard deviation a from the mean 706 along the X-axis 704. In other embodiments, any fractioning of the continuous field distribution 700 that enables performance of the process 400 determining missing values in respective incomplete data records 406 is performed. In some embodiments, samples are drawn from the bins 710 in a manner that facilitates collecting sufficient samples to attempt to simulate a relative distribution in order to see if candidates for the missing predictor can be found through a selection of the sampling values 414, i.e., one or more candidate predictors 420. Specifically, the data in the non-missing predictors 416 is analyzed to find sampling values 414 that may be related to the missing value(s), plot the sampling values 414 into the continuous field distribution 700/418 to find potential candidate predictors 420 based on where the sampling values 414 fall on the continuous field distribution 700/418. Accordingly, one or more candidate predictors 420 are determined from the continuous field distribution 700/418 of the sampling values 414 pulled from the non-missing predictors 416.

Referring to FIG. 8, a tabular diagram is provided illustrating an example of a categorical field distribution 800. Also referring to FIG. 4, in at least one embodiment, the categorical field distribution 800 (labeled as 422 in FIG. 4) of sampling values 414 for each field of non-missing values, i.e., non-missing predictors 416, is generated based on the population of non-missing predictors 416 in the training data, i.e., the respective complete data records 404. In at least some embodiments, values 802 of the non-missing predictors 416 with record-level percentages (%) 804 as a function of the counts 806 of the particular categories 808 "A" through "S" can be used to fit the categorical field distribution 800/422 of the non-missing predictors 416. The values 802 of the non-missing predictors 416, which define the categorization, are analyzed to determine if they are potential candidate values. For those values 802 that are determined to be potential candidate values, the potential candidate values are ranked with respect to predetermined factors, e.g., in some embodiments, without limitation, frequency of usage and semantic relationships determined through natural language processing analyses.

Also, in some embodiments, the top-ranked potential candidate values are selected as the candidate values, where such candidate values are determined to inherently have the highest likelihood of being satisfactory candidate predictors 418. In some embodiments, the top L categories are selected. As shown in FIG. 8, the top 14 categories 810 "A" through "N" are selected. Therefore, such embodiments use a categorical number threshold to determine selected candidate predictors 418 from the sampling values 414. In some embodiments, the cumulative sum of the top categories 810 may be considered, for example, and without limitation, the top 60%, as shown in cumulative categories 812 "A" through "M." Therefore, an overall percentile threshold may be used to determine selected candidate predictors 418 from the sampling values 414. These methods of selecting the uppermost categories facilitates further analysis of a percentage of the population within the categorical field distribution 800/422 through focusing on those majority values and ignoring the minority values. Therefore, one or more candidate predictors 420 are determined from the categorical field distribution 800/422 of the sampling values 414 pulled from the non-missing predictors 416. Accordingly, referring to FIGS. 4, 7, and 8, the candidate predictors 420 include those sampling values 414 that have been selected through the continuous field distribution 700/418 and the categorical field distribution 800/422.

Figure 9:
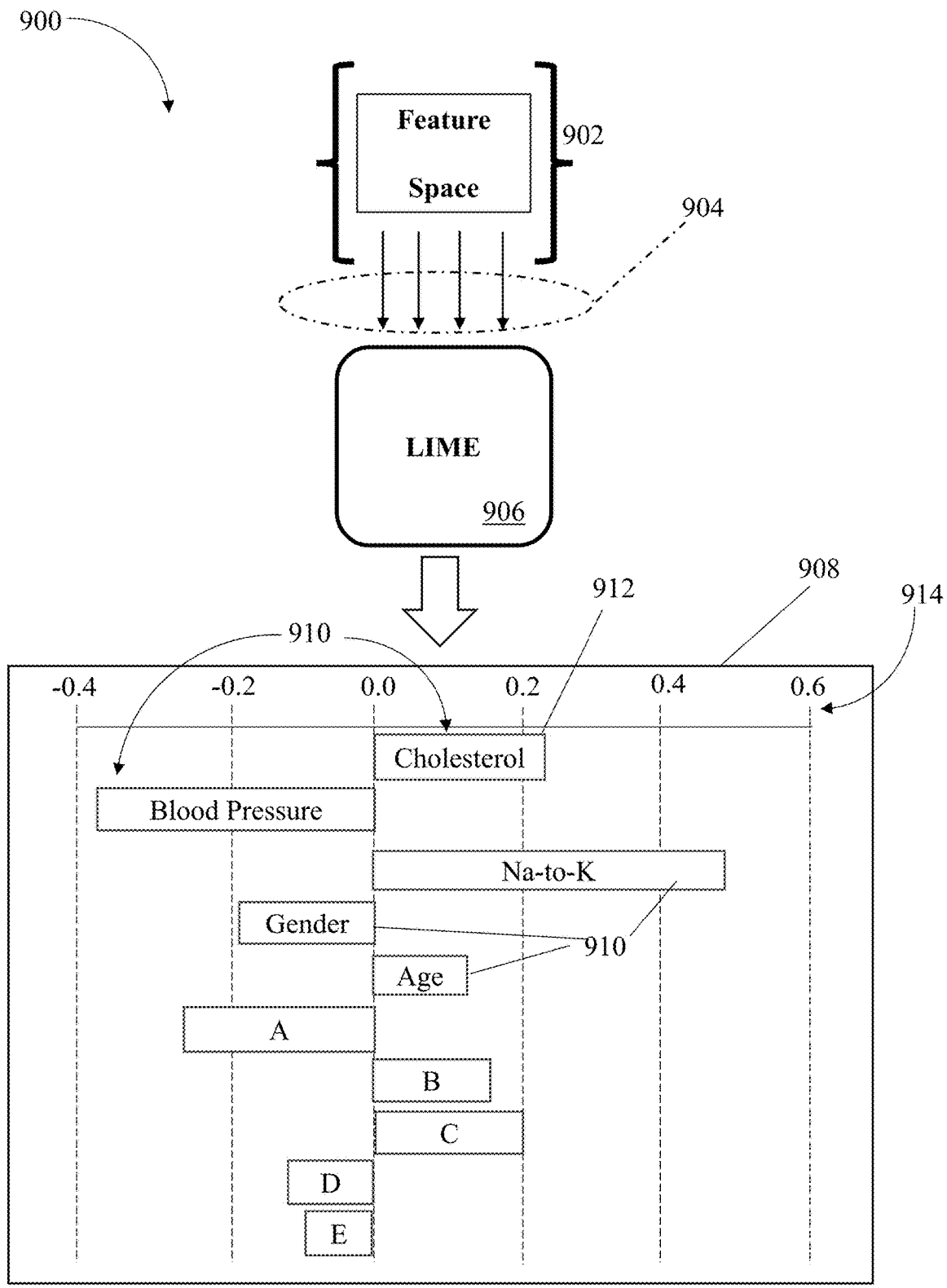
FIG. 9 is a schematic diagram illustrating a mechanism for determining a relative importance of candidate predictors, in accordance with some embodiments of the present disclosure.

Referring to FIG. 9, a schematic diagram is provided illustrating a mechanism 900 for determining a relative importance of the candidate predictors 904 (420 as shown in FIG. 4). Also, referring to FIG. 4. the values of the candidate predictors 904/420 populating the feature space 902 (412 in FIG. 4) are individually analyzed to determine a relative importance for each candidate predictor 904/420, thereby calculating a record-level predictor importance for each of the candidate predictors 904/420. In some embodiments, the mechanism 900 includes use of an algorithm for generating and documenting explanations of machine learning model classifications, such as, and without limitation, Local Interpretable Model-agnostic Explanations algorithm, i.e., LIME 906 (424 in FIG. 4). Each candidate predictor 904/420 in the feature space 902/412 is analyzed by LIME 906/424 to generate the record-level predictor importance of each candidate predictor 904/420. In one embodiment, LIME 906/424 perturbs the input of the candidate predictors 904/420 to determine how the candidate predictors 904/420 change in response to the perturbations. The respective changes to the candidate predictors 904/420 are at least partially indicative of the importance of the respective candidate predictor 904/420 relative to the rest of the candidate predictors 904/424.

Continuing to refer to FIGS. 4 and 9, a relative importance for each candidate predictor 904 is generated, where such analysis is presented herein in the form of a bar chart 908 for illustrative purposes. As shown in the bar chart 908, a plurality of candidate predictors 910 (substantially similar to the candidate predictors 904/420) labeled "cholesterol," "blood pressure," "Na-to-K," "gender," and "age" as well as nondescript "A" through "E" are presented as a bar 912 (only one labeled) to indicate a relative importance with reference to the relative importance scale 914 in unitless values extending from 0.0 to +0.6 and 0.0 to −0.4. In the illustrated embodiment, a potential for a physical malady is the basis for the relative importance values 914, where cholesterol and sodium-to-potassium measurements are most important in diagnosing the physical malady, age is less important, and blood pressure and gender are significantly less important. The numerical values for importance 914 are compared to a first threshold value and the top number (N) of candidate predictors 904/420 with the record-level predictor importance values 914 above the predetermined first threshold value are promoted for downstream analysis as a potential value, i.e., there will be N promoted candidate predictors 426 to address the missed predictors (e.g., those missed predictors 608 in FIG. 6) that will be evaluated as promoted candidate predictors 426 for the missing predictors 608. Accordingly, on a record-level basis, a subset of the candidate predictors 420 in the feature space 412 including promoted candidate predictors 426 is maintained based on the relative importance 914 thereof.

Referring again to FIG. 4, and as described the incomplete data records with the missing predictors 608 (see FIG. 6) are collected into a third dataset, i.e., an incomplete data record 406 dataset. Each incomplete data record 406 in the incomplete data record 406 dataset receives the respective promoted top N promoted candidate predictors 426 in turn from the feature space 412. Specifically, the respective promoted candidate predictors 426 are inserted into the respective cells (see FIG. 6) having the missing predictors 608, thereby creating a plurality of tentative data records 427 for each incomplete data record 406. The tentative data records 427 are collected into a fourth dataset, i.e., a tentative data records 427 dataset. The tentative data records 427 from the tentative data records 427 dataset are injected into the missing predictor predictive model 410, and each tentative data record 427 is scored by the missing predictor predictive model 410 with respect to establishing how well the respective tentative data record 427 fits with the complete data records 404 used to train the missing predictor predictive model 410. For example, in some embodiments, the target (see 606 of FIG. 6) of the respective tentative data record 427 is embedded within the respective tentative data record 427, therefore the actual value for the target 606 is known. The tentative data record 427 is processed within the missing predictor predictive model 410 to provide a computed target (not shown) that may be compared with the actual target 606. The closer the computed target is to the actual target 606, the greater the numerical value of the respective fit results 428 of the tentative data record 427 with the complete data records 404 within the respective data table (see 600 in FIG. 6). Accordingly, the fit results 428 of each comparison generates a confidence value 429 (also referred to as a comparison value 429) indicative of the inserted promoted candidate predictors 426.

FIG. 10 is a tabular diagram illustrating a best fit example ranking 1000. Also, referring to FIG. 4 as well, in some embodiments, once the respective fit results 428/comparison values 429 for fit for the tentative data records 427 are collected on a record-level basis, the fit results 428/comparison values 429 are ranked. In some embodiments, a first subset of fit scores are determined to be "best fit" by comparing the respective fit results 428/comparison values 429 with a predetermined second threshold value. Those tentative data records 427 with fit results 428/comparison values 429 in excess of the second threshold value will be identified as best fit data records 1004/432. The fit results 428/confidence values 429 are now referred to as classification probability values 1002/430, i.e., the classification probability values 430 of the respective promoted candidate predictors 426 being correct are indicative of being in the best fit data records 1004/432. Accordingly, the most likely values for the missing predictors are identified, and the effect of the tentative values for the missing predictors on the operation of a model to make predictions is recorded.

In addition, the reliability of the reasoning, or proper guesswork detail, is automatically recorded to justify the inclusion of the tentative values, i.e., the promoted candidate predictors 426 with a reasonable inference of good coverage with respect to the aforementioned, and respective, continuous field distribution 700 and categorical field distribution 800. The respective promoted candidate predictors 426 embedded in the best fit data records 1004 will also be established, and documented, as best fit for the missing predictor replacement predictors. Accordingly, one or more explanatory features directed toward the identification of the one or more best fit data records 1004 as a function of the respective inserted one or more promoted candidate predictors 426 are recorded to preserve the selections thereof, including the effects of the promoted candidate predictors 426 on the performance of the missing predictor predictive model 410.

FIG. 11 is a tabular diagram illustrating a worst fit example ranking 1100. Also, referring to FIG. 4 as well, in some embodiments, a second subset of fit scores are determined to be "worst fit" by comparing the respective fit results 428/comparison values 429 with a third threshold value. Those tentative data records 427 with fit results 428/comparison values 429 below the third threshold value will be identified as a worst fit data records 1104/434. The fit results 428/confidence values 429 are now referred to as classification probability values 1102/430, i.e., the classification probability values 430 of the respective promoted candidate predictors 426 not being correct are indicative of being in the worst fit data records 1104/432. Therefore, the least likely values for the missing predictors are identified, and the effect of the tentative values for the missing predictors on the operation of a model to make predictions is recorded. In addition, the reliability of the reasoning, or proper guesswork detail, is automatically recorded to justify the exclusion of the tentative values, i.e., the promoted candidate predictors 426 with a reasonable inference of poor coverage with respect to the aforementioned, and respective, continuous field distributions 700 and categorical field distribution 800. The respective promoted candidate predictors 426 embedded in the worst fit data records 1104 will also be established, and documented, as worst fit for the missing predictor candidate predictors. Accordingly, one or more explanatory features directed toward the identification of the one or more worst fit data records 1104 as a function of the respective inserted one or more promoted candidate predictors 426 are recorded to preserve the denials of selection thereof, including any deleterious effects of the promoted candidate predictors 426 on the performance of the missing predictor predictive model 410.

In one or more embodiments, one of the best fit data records 1004 is selected based on one or more of, and without limitation, other election criteria and user interaction. The selected best fit data record 1004 is inserted into the complete data records 404 to establish an updated complete data records dataset 436. In some embodiments, each incomplete data record 406 is analyzed and repaired in a serial fashion. In other embodiments, a plurality of incomplete data records 406 are analyzed and repaired in parallel. Also, in some embodiments, those incomplete data records 406 with multiple missing predictors are analyzed and repaired one missing predictor at a time. In other embodiments, those incomplete data records 406 with multiple missing predictors are analyzed and repaired substantially simultaneously.

The system, computer program product, and method as disclosed herein facilitate overcoming the disadvantages of and limitations of imputation. For those instances were imputation is not possible due to a lack of data, the disclosed process 400 as described herein determines candidates for missing values and selects the candidates with the best fit with respect to existing complete data records. The confidence level for the determined values is typically the highest for the set of candidate predictors evaluated and selected. In addition, the methods described herein provide individualized missing field importance for each given record, and may find replacements for multiple missing predictors in a data record. Moreover, in the event that the selected predictor values come into question, the methods described herein provide explanatory analysis for records with missing values, including record-level hypothetical explanations, reasonable guesswork on real values, and identified differences of candidate values from missing values.

Therefore, the embodiments disclosed herein provide an improvement to computer technology through providing one or more explanations of how a potential replacement or substitute value for a missing data value in a data record to be used for building a machine learning model, including how the candidate values could impact prediction results generated by the model once placed into production. In addition, rather than imputing values, the methods described herein generate candidate predictor values given information with no further inputs. Further, the methods performed as described herein function at a record-level.

The descriptions of the various embodiments of the present disclosure have been presented for purposes of illustration, but are not intended to be exhaustive or limited to the embodiments disclosed. Many modifications and variations will be apparent to those of ordinary skill in the art without departing from the scope and spirit of the described embodiments. The terminology used herein was chosen to best explain the principles of the embodiments, the practical application or technical improvement over technologies found in the marketplace, or to enable others of ordinary skill in the art to understand the embodiments disclosed herein.

What is claimed is:

1. A computer system comprising:
one or more processing devices and at least one memory device operably coupled to the one or more processing devices, the one or more processing devices are configured to:
receive a dataset, the dataset including a plurality of data records therein, wherein:
one or more data records of the plurality of data records are incomplete data records missing one or more predictors; and
one or more data records of the plurality of data records are complete data records;
train a model with at least a portion of the one or more complete data records;
generate one or more candidate predictors for the one or more missing predictors;
insert one or more respective promoted candidate predictors into the respective one or more incomplete data records, thereby creating one or more tentative data records;
inject the one or more tentative data records into the model;
and
select, subject to one or more scores from the model for the respective one or more injected tentative data records, a tentative data record from the one or more tentative data records for insertion into the complete data records.

2. The system of claim 1, wherein the one or more processing devices are further configured to:
generate a continuous field for a plurality of non-missing predictors from the dataset;
identify one or more first candidate predictors from the continuous field;
generate a categorical field for the plurality of non-missing predictors from the dataset;
identify one or more second candidate predictors from the categorical field; and
collect the one or more first candidate predictors and the one or more second candidate predictors within a feature space.

3. The system of claim 1, wherein the one or more processing devices are further configured to:
determine a predictor importance value for each candidate predictor of the one or more candidate predictors;
promote a portion of the candidate predictors that has a predictor importance value in excess of a first threshold value, wherein the inserted one or more respective candidate predictors comprise the promoted portion of the candidate predictors;

score each tentative data record of the one or more tentative data records, wherein the scoring facilitates establishing how well each tentative data record fits with the one or more complete data records, thereby determine a fit value for each of the one or more tentative data records, wherein the selected one or more tentative data records have a fit value exceeding a second threshold value; and
generate, subject to the scoring, a plurality of confidence values at least partially indicative of each respective inserted promoted candidate predictor's probability of being correct.

4. The system of claim 3, wherein the one or more processing devices are further configured to:
rank the plurality of confidence values numerically; and
determine a first subset of the plurality of confidence values, wherein the one or more processing devices are further configured to:
compare the numerical value of each confidence value of the plurality of confidence values with the second threshold value; and
select one or more tentative data records with a confidence value exceeding the second threshold value, thereby identifying one or more best fit data records.

5. The system of claim 4, wherein the one or more processing devices are further configured to:
determine a second subset of the plurality of confidence values, wherein the one or more processing devices are further configured to:
compare the numerical value of each confidence value of the plurality of confidence values with a third threshold value, the third threshold value less than the second threshold value; and
select one or more tentative data records with a confidence value less than the third threshold value, thereby identifying one or more worst fit data records.

6. The system of claim 4, wherein the one or more processing devices are further configured to:
automatically record one or more explanatory features directed toward the identification of the one or more best fit data records as a function of the respective inserted one or more candidate predictors.

7. The system of claim 1, wherein the one or more processing devices are further configured to:
populate the dataset with the one or more selected tentative data records to reduce a number of incomplete data records on a record-level basis.

8. A computer program product, comprising:
one or more computer readable storage media; and
program instructions collectively stored on the one or more computer storage media, the program instructions comprising:
program instructions to receive a dataset, the dataset including a plurality of data records therein, wherein:
one or more data records of the plurality of data records are incomplete data records missing one or more predictors; and
one or more data records of the plurality of data records are complete data records;
program instructions to train a model with at least a portion of the one or more complete data records;
program instructions to generate one or more candidate predictors for the one or more missing predictors;
program instructions to insert one or more respective candidate predictors into the respective one or more incomplete data records, thereby creating one or more tentative data records;

program instructions to inject the one or more tentative data records into the model;

program instructions to select, subject to one or more scores from the model for the respective one or more injected tentative data records, a tentative data record from the one or more tentative data records for insertion into the complete data records.

9. The computer program product of claim 8, further comprising:

program instructions to generate a continuous field for a plurality of non-missing predictors from the dataset;

program instructions to identify one or more first candidate predictors from the continuous field;

program instructions to generate a categorical field for the plurality of non-missing predictors from the dataset;

program instructions to identify one or more second candidate predictors from the categorical field; and program instructions to collect the one or more first candidate predictors and the one or more second candidate predictors within a feature space.

10. The computer program product of claim 8, further comprising:

program instructions to determine a predictor importance value for each candidate predictor of the one or more candidate predictors;

program instructions to promote a portion of the candidate predictors that has a predictor importance value in excess of a first threshold value, wherein the inserted one or more respective candidate predictors comprise the promoted portion of the candidate predictors;

program instructions to score each tentative data record of the one or more tentative data records, wherein the scoring facilitates establishing how well each tentative data record fits with the one or more complete data records comprising:

program instructions to determine a fit value for each of the one or more tentative data records, wherein the selected one or more tentative data records have a fit value exceeding a second threshold value; and program instructions to generate, subject to the scoring, a plurality of confidence values at least partially indicative of each respective inserted promoted candidate predictor's probability of being correct.

11. The computer program product of claim 10, further comprising:

program instructions to rank the plurality of confidence values numerically; and program instructions to determine a first subset of the plurality of confidence values, further comprising:

program instructions to compare the numerical value of each confidence value of the plurality of confidence values with the second threshold value; and program instructions to select one or more tentative data records with a confidence value exceeding the second threshold value, thereby identifying one or more best fit data records.

12. The computer program product of claim 11, further comprising:

program instructions to determine a second subset of the plurality of confidence values, further comprising:

program instructions to compare the numerical value of each confidence value of the plurality of confidence values with a third threshold value, the third threshold value less than the second threshold value; and program instructions to select one or more tentative data records with a confidence value less than the third threshold value, thereby identifying one or more worst fit data records.

13. The computer program product of claim 11, further comprising:

program instructions to automatically record one or more explanatory features directed toward the identification of the one or more best fit data records as a function of the respective inserted one or more candidate predictors.

14. A computer-implemented method comprising:

receiving a dataset, the dataset including a plurality of data records therein, wherein:

one or more data records of the plurality of data records are incomplete data records missing one or more predictors; and one or more data records of the plurality of data records are complete data records;

training a model with at least a portion of the one or more complete data records;

generating one or more candidate predictors for the one or more missing predictors;

inserting one or more respective candidate predictors into the respective one or more incomplete data records, thereby creating one or more tentative data records;

injecting the one or more tentative data records into the model; and selecting, subject to one or more scores from the model for the respective one or more injected tentative data records, a tentative data record from the one or more tentative data records for insertion into the complete data records.

15. The method of claim 14, wherein generating the one or more candidate predictors for the one or more missing predictors comprises:

generating a continuous field for a plurality of non-missing predictors from the dataset;

identifying one or more first candidate predictors from the continuous field;

generating a categorical field for the plurality of non-missing predictors from the dataset;

identifying one or more second candidate predictors from the categorical field; and collecting the one or more first candidate predictors and the one or more second candidate predictors within a feature space.

16. The method of claim 14, wherein determining the fit value for each of the one or more tentative data records comprises:

determining a predictor importance value for each candidate predictor of the one or more candidate predictors;

promoting a portion of the candidate predictors that has a predictor importance value in excess of a first threshold value, wherein the inserted one or more respective candidate predictors comprise the promoted portion of the candidate predictors;

scoring each tentative data record of the one or more tentative data records, wherein the scoring facilitates establishing how well each tentative data record fits with the one or more complete data records comprising:

determining a fit value for each of the one or more tentative data records, wherein the selected one or more tentative data records have a fit value exceeding a second threshold value; and generating, subject to the scoring, a plurality of confidence values at least partially indicative of each respective inserted promoted candidate predictor's probability of being correct.

17. The method of claim 16, wherein selecting a tentative data record with the fit value exceeding the second threshold value comprises:

ranking the plurality of confidence values numerically; and determining a first subset of the plurality of confidence values, comprising:

comparing the numerical value of each confidence value of the plurality of confidence values with the second threshold value; and selecting one or more tentative data records with a confidence value exceeding the second threshold value, thereby identifying one or more best fit data records.

18. The method of claim 17, further comprising:
determining a second subset of the plurality of confidence values, comprising:

comparing the numerical value of each confidence value of the plurality of confidence values with a third threshold value, the third threshold value less than the second threshold value; and selecting one or more tentative data records with a confidence value less than the third threshold value, thereby identifying one or more worst fit data records.

19. The method of claim 17, wherein selecting a tentative data record with the fit value exceeding the second threshold value comprises:

automatically recording one or more explanatory features directed toward the identification of the one or more best fit data records as a function of the respective inserted one or more candidate predictors.

20. The method of claim 14, wherein selecting a tentative data record with the fit value exceeding the second threshold value comprises:

populating the dataset with the one or more selected tentative data records to reduce a number of incomplete data records on a record-level basis.

* * * * *